(12) United States Patent
Fang et al.

(10) Patent No.: US 8,983,612 B2
(45) Date of Patent: *Mar. 17, 2015

(54) HIGH-FREQUENCY ELECTRICAL NERVE BLOCK

(71) Applicants: Zi-Ping Fang, Beachwood, OH (US); Jon J. Snyder, Kirtland, OH (US)

(72) Inventors: Zi-Ping Fang, Beachwood, OH (US); Jon J. Snyder, Kirtland, OH (US)

(73) Assignee: Neuros Medical, Inc., Willoughby, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/276,200

(22) Filed: May 13, 2014

(65) Prior Publication Data

US 2014/0249597 A1    Sep. 4, 2014

Related U.S. Application Data

(63) Continuation of application No. 13/474,926, filed on May 18, 2012, now Pat. No. 8,731,676.

(60) Provisional application No. 61/487,877, filed on May 19, 2011.

(51) Int. Cl.
  *A61N 1/00* (2006.01)
  *A61N 1/36* (2006.01)
  *A61N 1/05* (2006.01)

(52) U.S. Cl.
  CPC ............ *A61N 1/3606* (2013.01); *A61N 1/0556* (2013.01); *A61N 1/36071* (2013.01); *A61N 1/36153* (2013.01); *A61N 1/36157* (2013.01); *A61N 1/36171* (2013.01); *A61N 1/36021* (2013.01); *A61N 1/0551* (2013.01)

USPC .......................................................... 607/46

(58) Field of Classification Search
  CPC ........... A61N 1/36021; A61N 1/36071; A61N 1/3605; A61N 1/36017; A61N 1/056; A61N 1/05; A61N 1/0551
  USPC .......................................... 607/46, 116, 117
  See application file for complete search history.

(56) References Cited

U.S. PATENT DOCUMENTS

| | | |
|---|---|---|
| 3,738,368 A | 6/1973 | Avery et al. |
| 4,155,366 A | 5/1979 | Di Mucci |
| 4,573,481 A | 3/1986 | Bullara |
| 4,602,624 A | 7/1986 | Naples et al. |
| 4,979,511 A | 12/1990 | Terry, Jr. |
| 5,755,750 A | 5/1998 | Petruska et al. |
| 6,456,866 B1 | 9/2002 | Tyler et al. |
| 6,699,275 B1 | 3/2004 | Knudson et al. |
| 6,836,685 B1 | 12/2004 | Fitz |
| 6,860,851 B2 | 3/2005 | Knudson et al. |
| 7,167,750 B2 | 1/2007 | Knudson et al. |

(Continued)

FOREIGN PATENT DOCUMENTS

| | | |
|---|---|---|
| WO | 2005/105202 | 11/2005 |
| WO | 2009/058258 | 5/2009 |

OTHER PUBLICATIONS

Extended European Search Report EP12786360.3, mailed Sep. 19, 2014, 7 pages.

*Primary Examiner* — Christopher D Koharski
*Assistant Examiner* — Roland Dinga
(74) *Attorney, Agent, or Firm* — Thompson Hine LLP

(57) ABSTRACT

A method and apparatus that resulted in blocking an action potential in a nerve.

9 Claims, 8 Drawing Sheets

(56) References Cited

U.S. PATENT DOCUMENTS

| | | |
|---|---|---|
| 7,201,757 B2 | 4/2007 | Knudson et al. |
| 7,292,890 B2 | 11/2007 | Whitehurst et al. |
| 7,389,145 B2 | 6/2008 | Kilgore et al. |
| 7,444,183 B2 | 10/2008 | Knudson et al. |
| 7,783,362 B2 | 8/2010 | Whitehurst et al. |
| 7,860,570 B2 | 12/2010 | Whitehurst et al. |
| 8,060,208 B2 | 11/2011 | Kilgore et al. |
| 8,108,052 B2 | 1/2012 | Boling |
| 8,170,675 B2 | 5/2012 | Alataris et al. |
| 2002/0055779 A1 | 5/2002 | Andrews |
| 2002/0198572 A1 | 12/2002 | Weiner |
| 2003/0144709 A1 | 7/2003 | Zabara et al. |
| 2004/0243182 A1 | 12/2004 | Cohen et al. |
| 2005/0131485 A1 | 6/2005 | Knudson et al. |
| 2005/0143789 A1 | 6/2005 | Whitehurst et al. |
| 2005/0149154 A1 | 7/2005 | Cohen et al. |
| 2006/0195158 A1 | 8/2006 | Cory |
| 2006/0271137 A1 | 11/2006 | Stanton-Hicks |
| 2006/0293721 A1 | 12/2006 | Tarver et al. |
| 2008/0027505 A1* | 1/2008 | Levin et al. .................. 607/46 |
| 2008/0046055 A1 | 2/2008 | Durand et al. |
| 2008/0086180 A1 | 4/2008 | Ben-Ezra et al. |
| 2008/0183226 A1 | 7/2008 | Buras et al. |
| 2008/0294221 A1 | 11/2008 | Kilgore et al. |
| 2009/0083070 A1* | 3/2009 | Giftakis et al. .................. 705/2 |
| 2009/0204173 A1 | 8/2009 | Fang et al. |
| 2010/0152808 A1* | 6/2010 | Boggs, II .................. 607/46 |
| 2010/0211135 A1 | 8/2010 | Caparso et al. |
| 2010/0241190 A1 | 9/2010 | Kilgore et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0071593 A1 | 3/2011 | Parker et al. |
| 2011/0077721 A1 | 3/2011 | Whitehurst et al. |
| 2011/0230701 A1 | 9/2011 | Simon et al. |
| 2012/0016439 A1 | 1/2012 | Alataris et al. |
| 2012/0083709 A1 | 4/2012 | Parker et al. |
| 2012/0253261 A1* | 10/2012 | Poletto et al. .................. 604/20 |

* cited by examiner

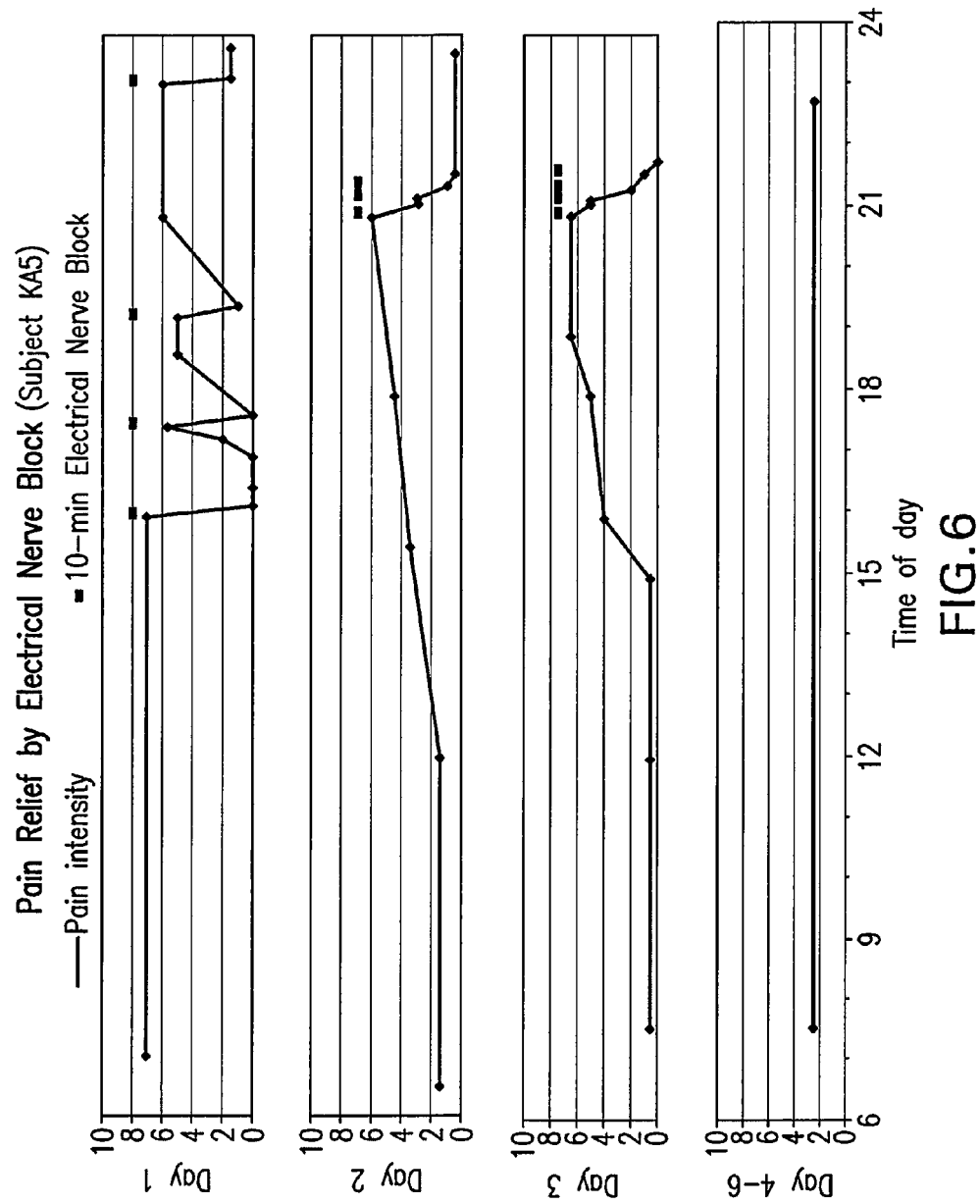

FIG 8: Summary of Feasibility Study Results
Electrical Nerve Block for Amputation Pain

| Subject | 1 | 2 | 3 | 4 | 5 |
|---|---|---|---|---|---|
| Gender, age | Male, 37 | Male, 54 | Female, 53 | Male, 76 | Male, 52 |
| Cause of amputation | Dysvascular | Dysvascular | Infection | Trauma | Trauma |
| Level of Amputation | Below knee | Above knee | Above knee | Below knee | Above knee |
| Nerve blocked | Tibial | Sciatic | Sciatic | Tibial | Sciatic |
| Spontaneous pain intensity at each visit | 3, 3, 3 | 0, 0, 0, 0 | 0, 0 | 2, 3, 7, 7 | 0, 7, 7 |
| Induced pain intensity by pressing the neuroma | Not tried | 9 | 7 | 5 | 8 |
| In-clinic test result: number of sessions with significant/partial/no pain reductions | 1 / 2 / 5 | 3 / 1 / 2 | 0 / 3 / 1 | 6 / 1 / 0 | 7 / 0 / 0 |
| At-home use result: number of sessions with significant/partial/no pain reductions | 0 / 0 / 1 | Not used | Not used | 13 / 0 / 0 | 4 / 0 / 0 |
| Conclusion | Success in clinic | Success in clinic | Not successful | Complete success | Complete success |

HIGH-FREQUENCY ELECTRICAL NERVE BLOCK

This application is a continuation of pending U.S. application Ser. No. 13/474,926, filed May 18, 2012, which claims priority to U.S. application Ser. No. 61/487,877 filed May 19, 2011, each of which is expressly incorporated by reference herein in its entirety.

In one embodiment, successful results are disclosed from a method and apparatus that uses high frequency nerve block to acutely treat peripheral pain, either acute pain or chronic pain (more than 6 months in duration), in humans by blocking nerve conduction of an action potential. Acute treatment is defined as on demand treatment with substantially immediate pain relief effect. In one embodiment, the method is used in peripheral nerves having a diameter up to about 12 mm, i.e., in relatively large nerves such as the sciatic nerve. In one embodiment, the method is used on a nerve to ameliorate a non-pain condition by therapy to a nerve, e.g., motor nerves resulting in spasticity, e.g., nerves providing an urge to void in overactive bladder.

Previous therapy for pain of peripheral origin, e.g., damaged nerves in a limb, consisted of one or a combination of the following methods.

One previous therapy was local injection of a pharmacologic anesthetic such as lidocaine. The therapeutic effect often lasts only a short time, e.g., a few hours. Repeated dosing is typically not feasible because of toxicity of the anesthetic and other reasons.

Another previous therapy was conventional electrical stimulation by surface electrodes or surgically implanted electrodes (e.g., TENS, Peripheral Nerve and Spinal Cord Stimulator). Electrical stimulation therapy is used to treat back pain and joint pain, but produces inconsistent effects. The inconsistencies are due to the indirect nature of the therapy; instead of blocking pain signals from the origin of the pain, this type of electrical stimulation activates non-pain sensory nerves to generate other types of sensation (e.g., tingling) that mask the pain sensation. Such masking is by a complex, and often unreliable, interaction of various parts of the nervous system.

A potential therapy involves reversibly blocking peripheral nerves by applying high frequency alternating current directly on a nerve trunk. Specifically, a current ranging from 5 kHz to 50 kHz was applied; this was denoted as high frequency, compared to a current of less than 1 kHz applied in the conventional electrical stimulation described above. Efficacy of the high frequency alternating current therapy in acute non-human animal experiments (frog, cat) has been reported. U.S. Pat. Nos. 7,389,145 and 8,060,208 describe in general this electrical stimulation technology. No data are described.

One embodiment of the invention discloses a method for reversibly blocking an action potential in a peripheral nerve having a diameter exceeding 3 mm and up to about 12 mm, e.g., a sciatic nerve, a tibial nerve, etc., in a patient in need thereof. The method comprises providing an electrical waveform for an interval of time sufficient to effect substantially immediate pain relief, defined generally as within about 10 min. One embodiment uses a waveform ranging from 5 kHz to 50 kHz. One embodiment uses a 10 kHz sinusoidal waveform at a current ranging from 4 mApp to 26 mApp. The electrode can be retained in a cuff encircling the desired peripheral nerve in which the action potential is to be blocked; the cuff inner diameter may range from about 5 mm to about 12 mm. The time interval may be about 10 minutes, but an interval may be selected by a magnitude sufficient to effect pain relief in the patient. In one embodiment, the electrical waveform to effect pain relief ranges from a voltage from 4 Vpp to 20 Vpp, or a current ranging from 4 mApp to 26 mApp. The time of increasing magnitude can range from about 10 seconds to about 60 seconds with a steady ramp up of voltage or current. The waveform is provided by a waveform generator that is operatively connected to the electrode implanted in the patient; such methods are known in the art.

One embodiment is a device that reversibly blocks an action potential in a relatively large nerve, i.e., a nerve with a diameter exceeding about 3 mm and up to 12 mm. The apparatus has a self-curling sheet of non-conductive material that includes a first layer, which is pre-tensioned, and a second layer, which is not pre-tensioned. The two layers are configured to form a cuff containing or holding strips of conducive material therebetween. In embodiments, the device has one, two, three, four or more continuous strips of a conductive material that are disposed adjacent, but not transverse, to one longitudinally extending edge of the self-curling sheet, each of these strips of conductive material is connected to an electrically conductive lead. In one embodiment, the device contains one strip of a conductive material, termed a monopolar configuration. In one embodiment, the device contains at least two continuous strips, connected by an electrically conductive lead, of a conductive material, termed a bipolar configuration. In one embodiment, the device contains at least three continuous strips, connected by an electrically conductive lead, of a conductive material, termed a tripolar configuration. In one embodiment, the device contains at least four continuous strips, connected by an electrically conductive lead, of a conductive material. Multiple apertures, typically circular but not necessarily so limited in shape, are disposed at periodic intervals of the inner nerve-contacting surface along the curling length of one of the two non-conductive sheets or layers of the self-curling sheet/cuff. This provides contact to the nerve by exposing and providing continuous multiple conductive contact points. The exposure may be at any interval that exposes as much of the conductive material as possible or desirable, and exceeds the contact surface area of conventional electrodes. Each of the first or top non-conductive sheet or layer and the second or bottom non-conductive sheet or layer still retains and contains the conductive material therebetween, i.e., sandwiched inside the sheets or layers, so that the conductive material is in fact retained and does not pop out or come out while providing efficient current delivery. In one embodiment the non-conductive material is silicon, the electrically conductive lead is stainless steel, and the conductive material is platinum. Other materials for each of the non-conductive material, the electrically conductive lead or wire, and the conductive material are known in the art. In use, the device is operatively connected, e.g., by an external lead or wire, to a waveform generator that provides the regulated waveform.

One embodiment is a method for treating peripheral nerve pain in a patient in need of this treatment. The above-described device encircled a particular segment of a targeted peripheral nerve, e.g., a sciatic nerve, a tibial nerve. Using a patient-implanted electrode connected to an electrical waveform generator, an electrical waveform is applied for a time interval, e.g., 10 min, sufficient to effect substantially immediate patient pain relief, e.g., within 10 min, and an extended period of pain relief up to several hours. The current in one embodiment ranges from 4 mApp to 26 mApp, and in one embodiment ranges from 4 mApp to 26 mApp.

In the inventive method, data from a human study using high frequency electrical nerve block technology for pain management are provided. In one embodiment, the result was that amputation pain was reduced. Application of 10 kHz alternating current generated by a custom generator via a custom implanted nerve electrode significantly reduced pain in the majority of patients treated by the method. The required voltage/current level is reported. The duration for achieving reliable pain relief in specific human nerves is reported. The required sequence and time to apply the electrical energy to minimize side effects is reported. The anticipated accompanying sensations and their time course is reported. The duration of pain relief after termination of the electrical current is reported. The cumulative effect of successive applications of the current on the extent of pain reduction is reported.

The apparatus was an implantable electrode operatively connected to an external or implanted waveform generator. The electrode was a spiral cuff electrode similar to that described in U.S. Pat. No. 4,602,624, more fully described below. In use, the electrode was implanted in a human mammal on a desired peripheral nerve trunk proximal to the pain source (e.g., a neuroma), such that the cuff encircled the desired peripheral nerve in which the action potential was to be blocked. The cuff inner diameter ranged from about 5 mm to about 12 mm. The sciatic nerve is known to have a relatively large nerve trunk; the diameter of the proximal part of the sciatic nerve in a human adult is about 12 mm. In one embodiment, the apparatus and method was used on the sciatic nerve to treat limb pain in above knee amputees. In one embodiment, the apparatus and method was used on the tibial nerve to treat limb pain in below knee amputees.

BRIEF DESCRIPTION OF THE DRAWINGS

FIG. 6 graphs one patient's pain intensity and pain relief using the invention.

FIG. 8 tabulates treatment outcomes from five patients.

Figure 1:
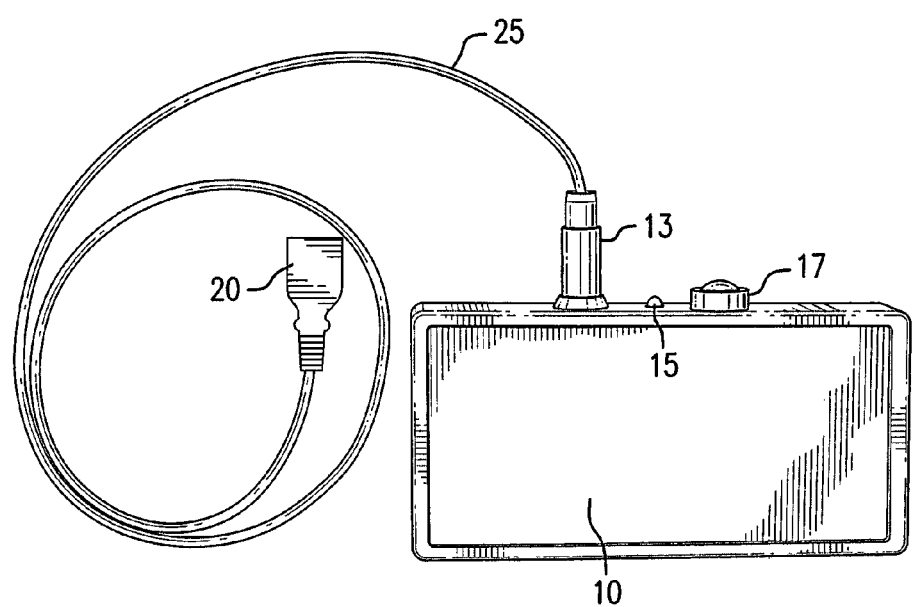
FIG. 1 is a perspective view of an external waveform generator and interconnection cable.
Figure 2:
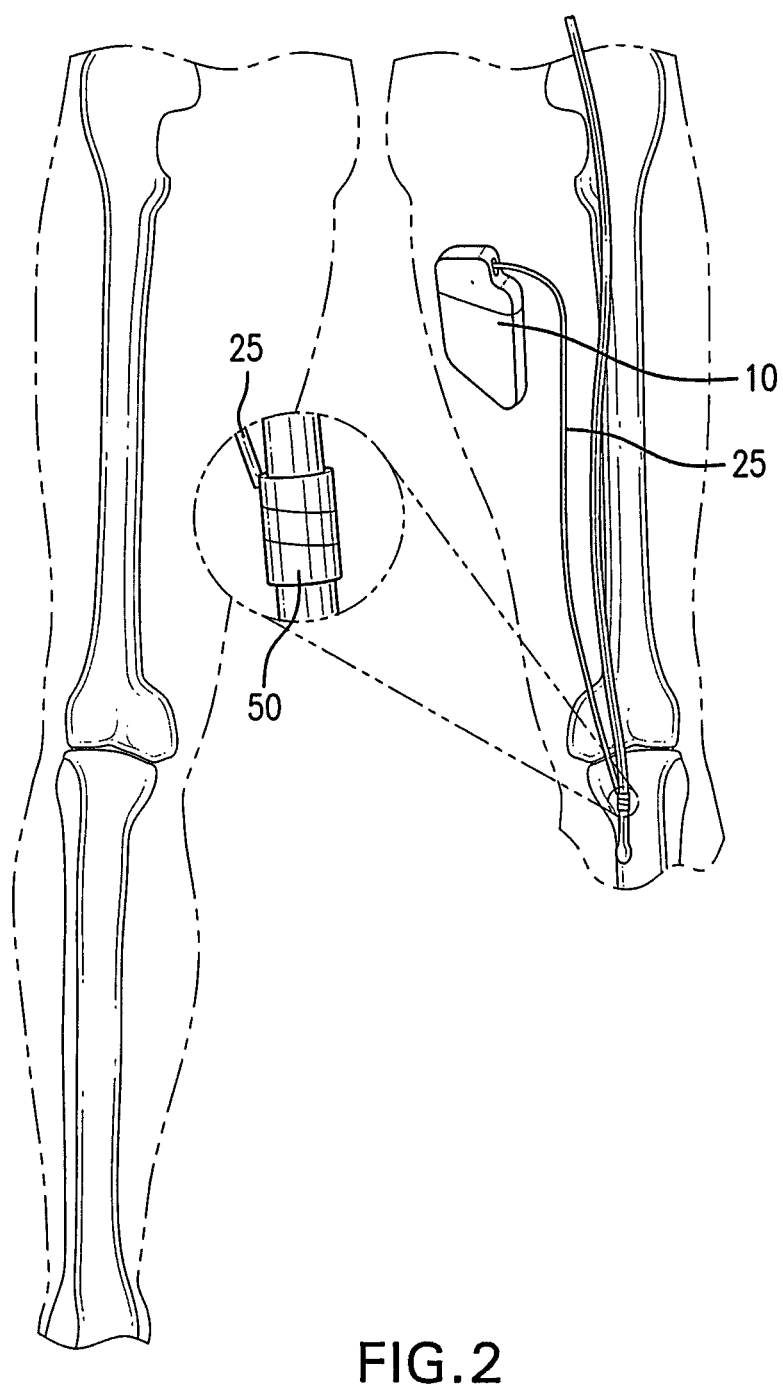
FIG. 2 shows an in-use implanted waveform generator operably connected to a nerve cuff electrode encircling a patient's nerve.

In use, the external and implanted waveform generator, shown in FIGS. 1 and 2 respectively, delivered high frequency alternating current in any form (sinusoidal wave, rectangular, other shape) sufficient to block the nerve action potential. In use, the operator selectively regulated the amount of current applied to the electrode, the duration, and any other desired parameters (e.g., continuous versus intermittent), etc. for therapy. In one embodiment, a sinusoidal waveform frequency of 10 kHz effectively and repeatedly reduced pain. In one embodiment, a sinusoidal waveform frequency ranging from 20 kHz to 30 kHz effectively reduced pain, but required about two times higher voltage and higher current for a 20 kHz sinusoidal waveform, and about three times higher voltage and higher current for a 30 kHz sinusoidal waveform, compared to that required for a 10 kHz sinusoidal waveform.

Using a sinusoidal waveform frequency of 10 kHz, patients reported a sensation threshold at a voltage ranging from 1 Vpp to 10 Vpp, and at a current ranging from 1 mApp to 16 mApp. The sensation threshold was the minimum stimulation at which a patient indicated that s/he feels a sensation due to the applied current, e.g., a patient may feel a tingling sensation.

Indication of a sensation threshold does not indicate pain relief, which is defined broadly as any pain mitigation or amelioration including but not limited to complete pain relief. Using a sinusoidal waveform of 10 kHz, the patient's relief from pain was achieved at a voltage ranging from 4 Vpp to 20 Vpp, and at a current ranging from 4 mApp to 26 mApp. The interval between the two parameters (the voltage/current required to be applied to achieve a sensation threshold, versus the voltage/current required to be applied to achieve pain relief) was optimally achieved by a conservative steady ramping up over a range from about 10 seconds to about 60 seconds. This minimized or prevented the patient from experiencing pain or other undesirable sensations at the outset of therapy.

Figure 3B:
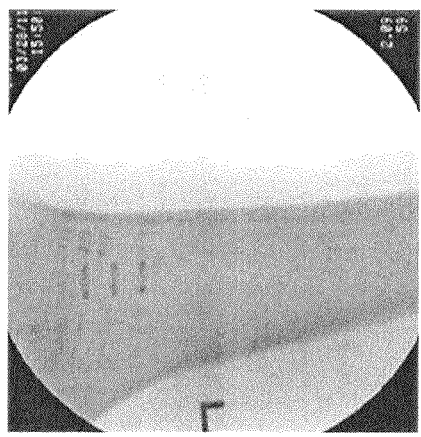
FIGS. 3A, 3B are a photograph on the implanted cuff and electrode, and a confirmatory fluoroscopy image of same, respectively.
Figure 3A:
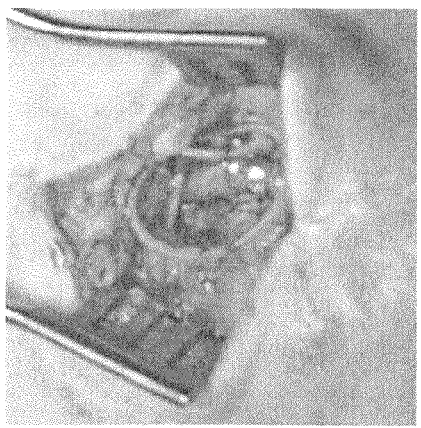

In one embodiment, the electrode was implanted on the tibial nerve, as shown in FIG. 3A. Proper implantation was verified by fluoroscopy visualization, as shown in FIG. 3B.

In one of five patients experiencing pain post lower-limb amputation, the extent of baseline pain intensity and relief of this pain by a self-administered narcotic pill were compared to the extent of each of baseline pain intensity and relief of this pain using the disclosed nerve block apparatus and method was self-assessed over a 21 consecutive day period. The patient self-assessed pain intensity using a 0-10 scale where 0 is no pain and 10 is as bad as it could be. The narcotic was hydrocodone/APAP formulated as a tablet at a dose of 10 mg/325 mg. The patient self-administered the tablet orally as needed.

When self-administering the electrical nerve block therapy, the parameters over which the patient did not have control were the amount of current applied, and the duration of each administration period. The parameters over which the patient did have control were the time(s) during the 24 hour period to self-administer the therapy, and the time interval between the administrations. In one embodiment, each treatment was for 10 minutes. In one embodiment, one self-administered electrical treatment for 10 minutes was immediately followed by at least one additional self-administered electrical treatment for 10 minutes to result in cumulative pain reduction effect. The amount of current/voltage applied during each interval ranged from 4 mApp to 26 mApp/4 Vpp to 20 Vpp, respectively.

Figure 5:
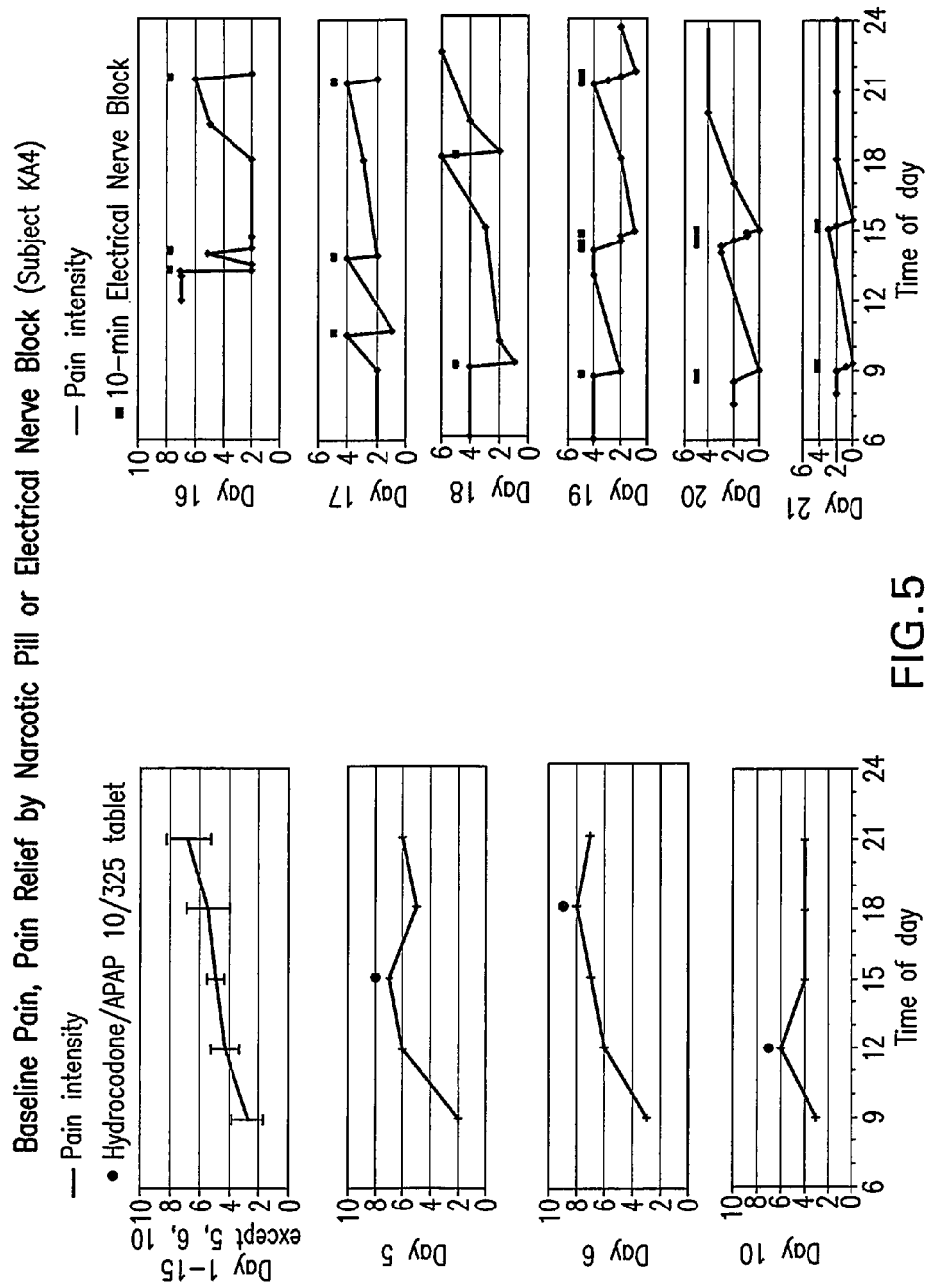
FIG. 5 graphs one patient's pain relief comparing use of the invention versus drug treatment.

Specific selected data for each of two patients are shown in FIGS. 5 and 6 respectively. A summary of the results for all of the five patients is shown in FIG. 8.

The patients reported that they experienced pain mitigation within minutes of treatment onset. The patients reported that sensations such numbness, tingling, and pulling, subsided within minutes after treatment onset. The patients reported that, after a 10 min treatment (application of electrical blocking current), they experienced pain reduction that was sustained up to several hours after cessation of treatment.

A description of various embodiments of the electrode used for nerve conduction block is as follows. They differ from the use of the apparatus disclosed in Naples U.S. Pat. No. 4,602,624. Naples' electrode is used to stimulate, i.e., excite, activate, generate, an action potential in a nerve having a diameter of about 1 mm to about 3 mm. In Naples, four sets of rectangular-shaped electrodes constitute the contact points that are sandwiched between two layers of a non-conductive material such as silicon. The layers of non-conductive material were self-curling. The conductive contact points were disposed at uniform intervals therebetween at sites on the inner circumference of a first resiliently extensible layer. The conductive contact points are connected by conductive wires or leads, e.g., stainless steel wires. The layers have openings (windows) in the non-conductive material to expose the conductive contact points to the nerve upon selective regulation, in this case, activation to initiate an action potential. The distance between the openings (separation distance) and curling length of the layers is proportional to the nerve diameter.

In attempting to block an action potential in nerves having a diameter exceeding about 3 mm, the previously described apparatus and method is inadequate. This is because a simple scale-up of the aforementioned design did not permit adequate current flow that is necessary to block conduction of an action potential in a nerve that has a relatively larger diameter as compared to a typical nerve which has a diameter that does not exceed about 3 mm. For example, the sciatic nerve in an adult human has a diameter exceeding about 3 mm; it can be up to 12 mm diameter. The sciatic nerve is a frequent source of pathology and often requires therapy. The inventive method was used on nerves having a diameter exceeding about 3 mm for nerve conduction block.

In one embodiment the inventive method was used on nerves having a diameter between about 1 mm and about 8 mm. In one embodiment the inventive method was used on nerves having a diameter between about 3 mm and about 10 mm. In one embodiment the inventive method was used on nerves having a diameter between about 8 mm and about 12 mm. In one embodiment the inventive method was used on nerves having a diameter up to about 12 mm. The inventive method blocked an action potential in a nerve, including the sciatic nerve, and thus ameliorated and/or mitigated peripheral nerve pain. The inventive method was not used to generate an action potential in a nerve; rather, it was used to block conduction of an action potential. Blocking conduction of an action potential in a nerve, versus stimulating an action potential in a nerve, requires higher current, and hence lower resistance, at the interface between the nerve and the electrode. The inventive method used a generator that advantageously provided adequate voltage with lower power consumption. The inventive method thus minimized thermal damage to tissue from heat that was generated during its use, while providing improved efficiency.

In all embodiments, the electrode had a relatively larger contact surface with the nerve than conventional electrodes, such as Naples' electrode. As only one illustrative example used in the inventive method, the apertures were spaced at an interval ranging from 0.5 mm up to 1.9 mm. In one embodiment, the apertures were spaced at 1.0 mm intervals, defined as a center-to-center dimension between neighboring apertures.

Figure 4:
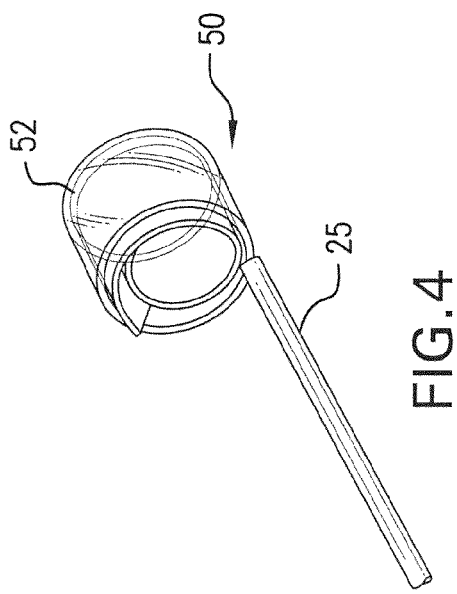
FIG. 4 schematically shows the nerve cuff electrode and lead.
Figure 7A:
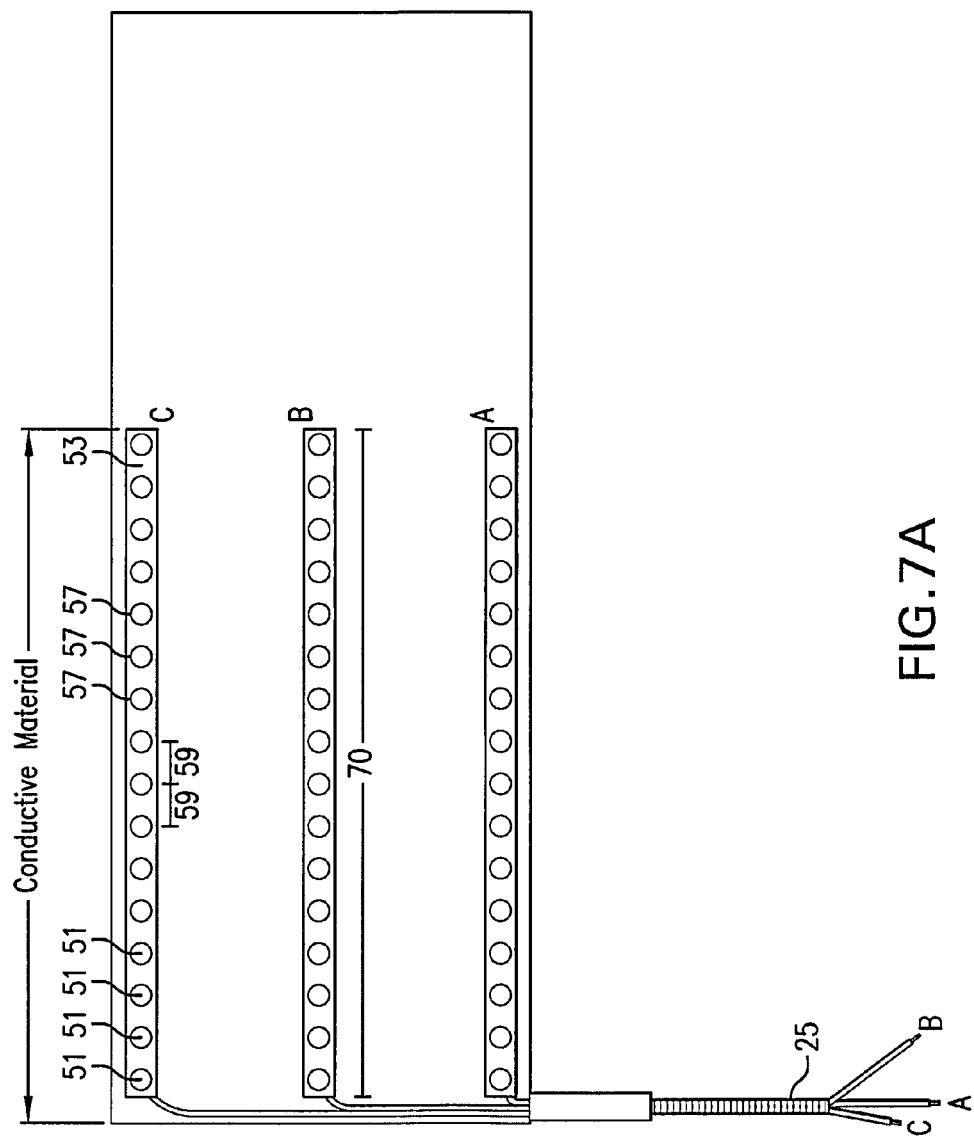
FIG. 7A shows a general schematic of a tripolar electrode in an uncurled configuration.
Figure 7B:
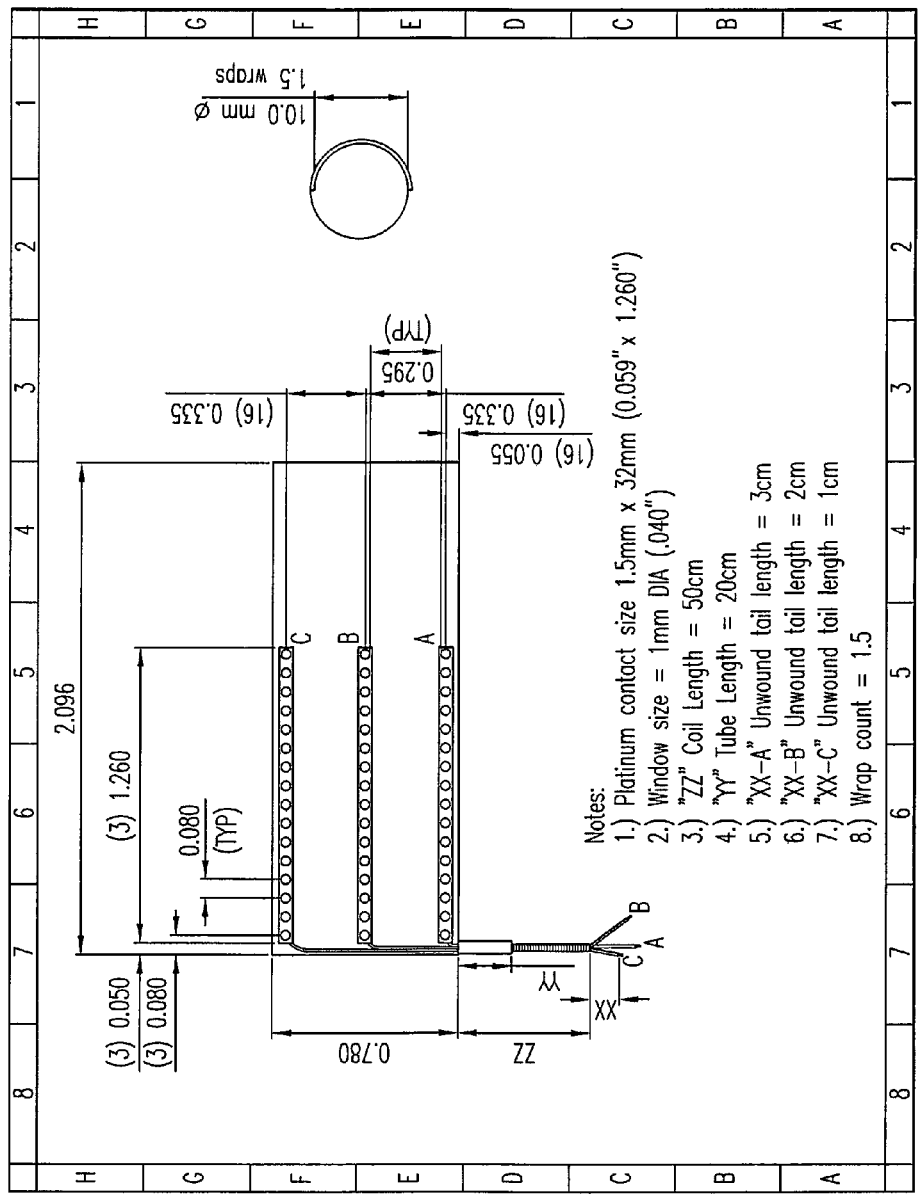
FIG. 7B shows one embodiment of FIG. 7A with specific dimensions.

As shown in FIG. 1, an external waveform generator 10 had an electrode connector 20 operatively connected with cable 25, having connector 13, LED indicator 15, and on/off indicator 17. As shown in use in FIGS. 2, 3, and 4, nerve cuff electrode 50 had conductive material 51 contained in self-curing sheet 53 and lead 25 to connect to the waveform generator 10. As best shown in FIGS. 7A, 7B, the conductive material 51 was both contained and retained within an implantable expandable spiral cuff 52, shown in FIG. 4. The cuff 52 provided the flexibility required for use to contact and regulate nerves having a diameter exceeding about 3 mm and up to about 12 mm, and provided a non-rigid contact surface with the nerve in order to minimize tissue damage.

In one embodiment, shown in general FIG. 7A and in one specific embodiment shown in FIG. 7B, the electrode contained continuous strips of conductive material 51, specifically platinum in FIG. 7B, in a sandwich configuration, with two opposing surfaces or sheets of a non-conductive material 53, specifically silicon in FIG. 7B, along the entire length of the non-conductive material 53. The non-conductive material 53 was self-curling. To provide points of contact of conductive material 51 with the nerve, around which the cuff 52 was implanted, openings or apertures 57 were created in one surface of the non-conductive material 53 at periodic intervals 59. The spacing of the intervals 59 is such that the conductive material 51 was contained and retained within the non-conductive material 53 during use, i.e., the non-conductive material does not pop out or come out, and provides sufficient exposure of the conductive material 51 for electrical contact with the nerve. In one embodiment, the openings 57 were created at 1 mm intervals. In one embodiment, the openings 57 were created at intervals ranging between about 1 mm to about less than 2 mm. The openings 57 were created in the non-conductive material 53; it was at these openings 57 that the nerve was exposed to the conductive material 51 in order to block conduction of an action potential. In a bi- or tri-polar embodiments, the distance or spacing between strips is 1:1 depending upon the nerve size to be treated; larger sized nerves can accommodate larger space between the strips. In FIG. 7A, for each electrode, the strip length with conductive material contacts 70 is shown for each of leads or wires A, B, and C. This electrode design achieved efficient current delivery to effect this blockage of the action potential. This electrode design contained and retained the conductive material 51 within the two layers of non-conductive material 53.

In one embodiment, the curled configuration of the apparatus had a diameter of 10 mm with a 1.5 wrap, meaning that one half of the circumference contained a single sandwiched sheet (i.e., 2 layers) of non-conductive material 53, and the other 1.5 wrap of the circumference contained two sandwiched sheets (i.e., 4 layers) of non-conductive material 53. Any wrap resulting in a compliant, flexible cuff that does not damage the nerve may be used. The interpolar distance was about 0.75 times to 1.5 times the inner cuff diameter. The contact surface area was relatively larger than the contact surface area of conventional electrodes, such as the electrode Naples disclosed for nerve stimulation and activation, safely delivered the required higher amount of charge to block the nerve action potential, even in nerves up to 12 mm in diameter.

In one embodiment, the electrode was bipolar. In another embodiment, the electrode used three contact groups, i.e., tripolar. In this embodiment, the electrode contained three continuous strips of conductive material, connected by electrically conductive leads (A, B, C in FIGS. 7A, 7B), that was provided between the two opposing non-conductive surfaces in the same manner as described above for two continuous strips of conductive material. The separation, i.e., distance, between the two, three, or more conductor bands is a function of the diameter of the cuff. The ratio of separation:diameter ranged between 0.75:1.5.

The above-described electrode blocked numerous nerve fascicles and/or nerve fibers. The blockage was reversible; the cuff was implantable along any length of nerve at any site, and electrical parameters (current, voltage, duration, etc.) were selected by the operator. In one embodiment, the recipient of the implantable apparatus is the operator. In one embodiment, a health care professional is the operator. Use of the electrode results in lower resistance at the interface between the nerve and the electrode. Such multiple points of contact, and relatively large openings, enables the electrode to block at least one portion of the nerve trunk. In the embodiment with a tripolar configuration, the electrode can be used to first block at least one portion of the nerve trunk, and then stimulate the other portion to verify blockage.

The inventive method has use in a variety of pain and non-pain applications. One embodiment uses the method and electrode to block peripheral nerve pain. Besides use to ameliorate amputation pain, the uses and description of which was previously described, other examples of ameliorating pain include, but are not limited to, ameliorating neuropathic pain, nociceptive pain, chronic neurogenic pain, migraine pain, post-herpetic neuralgia, pelvic pain, chronic post-surgical pain, post-surgical pain, and neuralgia. As known in the art, pain is defined as an unpleasant sensation caused by noxious stimulation of the sensory nerve endings. Amputation pain is pain resulting from the surgical removal of a part of the body or a limb or a part of a limb to treat for therapy resulting from, e.g., pathology, trauma, etc. Neuropathic pain is pain that results from the direct inputs of nervous tissue of the peripheral or central nervous system, generally felt as burning or tingling and often occurring in an area of sensory loss. Nociceptive pain is pain that results from stimulation of the neural receptors for painful stimuli, i.e., inputs of nociceptors. Chronic neurogenic pain is pain that originates in the nervous system and persists over time (i.e., not acute but chronic). Migraine pain result in headaches and is related to dilation of extracranial blood vessels, the origin of which may be defined (e.g., consumption of certain foods, external stimuli) or may be unknown. Post-herpetic neuralgia is a form of neuralgia with intractable pain that develops at the site of a previous eruption of herpes zoster. Pelvic pain is pain that is centered in the pelvis region i.e. lower part of the trunk of the body. Chronic post-surgical pain is pain persisting for a long period of time beginning after treatment of disease or trauma by manipulative and operative methods. Post-surgical pain is pain beginning after treatment of disease or trauma by manipulative and operative methods. Neuralgia is pain, often severe and characterized as "stabbing", resulting from any number of nervous system pathologies or disorders.

In other embodiments, the inventive method is used in non-pain applications where blocking the action potential of a nerve provides the desired amelioration outcome. One example of such a non-pain use is in ameliorating obesity. As known in the art, obesity is an abnormal increase in the proportion of fat cells, mainly in the viscera and subcutaneous tissues. The inventive method may be used on the vagus nerve in this embodiment. Another example of such a non-pain use in ameliorating overactive bladder, which is a colloquial term for bladder storage function disorders or pathologies. The method and electrode can be used on the pelvic nerve to ameliorate the sudden urge to void that may be difficult to suppress and may lead to incontinence. Another example of such a non-pain use is in ameliorating spasticity of any motor nerve; spasticity results in excessive muscle contraction and can be due to any of several nervous system disorders. The following hypothetical examples illustrate these embodiments.

A patient with advanced type 2 diabetes is experiencing neuropathic pain in his feet as a result of loss of blood flow to his legs. Normal doses of pain-killing narcotics are either ineffective or cause undesirable side effects. After implantation of the electrode and placement of the cuff on the right sciatic nerve trunk at the popliteal fossa, the patient self-treats pain for 10 minutes at 10 mApp, experiencing immediate pain relief. The patient repeats the procedure on demand, as needed.

A migraine patient experiences severe headaches unresponsive to conventional treatment. After implantation of the electrode and placement of the cuff on the greater occipital nerve trunk, the patient self-treats pain for 10 minutes at 10 mApp, experiencing immediate pain relief. The patient repeats the procedure on demand, as needed.

A patient with shingles experiences postherpetic neuralgia, unresponsive to conventional treatment. After implantation of the electrode and placement of the cuff on the intercostal nerves, the patient self-treats pain for 10 minutes at 10 mApp, experiencing immediate pain relief. The patient repeats the procedure on demand, as needed.

A post-operative inguinal hernia repair patient experiences chronic pain. After implantation of the electrode and placement of the cuff on the ilioinguinal nerve, the patient self-treats pain for 10 minutes at 10 mApp, experiencing immediate pain relief. The patient repeats the procedure on demand, as needed.

A patient with overactive bladder syndrome undergoes a procedure for implantation of the electrode and placement of the cuff on the pelvic nerve. The patient self-treats at 10 mApp upon an urge to urinate, experiencing urge cessation.

A patient with muscle spasticity undergoes a procedure for implantation of the electrode and placement of the cuff on a motor nerve. The patient self-treats at 10 mApp when needed, ameliorating spasticity of the muscle to which the nerve innervates The embodiments shown and described are specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A method of ameliorating sensory nerve pain in a patient in need thereof, the method comprising
   (a) connecting a waveform generator operatively to an implanted electrode contacting a trunk of a sensory peripheral nerve in the patient resulting in prevention of action potential transmission in the nerve upon application of a waveform of at least 5 kHz up to 50 kHz where the frequency blocks but does not stimulate and is not used to generate an action potential in a nerve but rather to block conduction of an action potential at one of a voltage ranging from 4 V peak to peak (Vpp) to 20 Vpp, or a current ranging from 4 mA peak to peak (mApp) to 26 mApp at a plurality of contact surfaces with the nerve trunk for an interval sufficient to effect substantially immediate pain relief in the patient, and
   (b) optionally repeating step (a) as needed to ameliorate nerve pain.

2. The method of claim 1 where the waveform provided is a sinusoidal waveform at 10 kHz.

3. The method of claim 1 where the nerve diameter is up to 12 mm.

4. The method of claim 1 applied to an ilioinguinal nerve to ameliorate post-surgical hernia pain.

5. The method of claim 1 applied to an intercostal nerve to ameliorate pain from shingles.

6. The method of claim 1 applied to a sciatic nerve to ameliorate neuropathic diabetes pain.

7. The method of claim 1 applied to an occipital nerve to ameliorate migraine pain.

8. The method of claim 1 where the interval is controlled by the patient.

9. A method of ameliorating overactive bladder in a patient in need thereof, the method comprising
   (a) connecting a waveform generator operatively to an implanted electrode contacting a trunk of a pelvic nerve in the patient resulting in prevention of action potential transmission in the nerve upon application of a waveform of at least 5 kHz up to 50 kHz where the frequency blocks but does not stimulate and is not used to generate an action potential in a nerve but rather to block conduction of an action potential at one of a voltage ranging from 4 Vpp to 20 Vpp, or a current ranging from 4 mApp to 26 mApp at a plurality of contact surfaces with the nerve trunk for an interval sufficient to effect substantially immediate amelioration, and (b) optionally repeating step (a) as needed.

* * * * *